(12) United States Patent
Vick, Jr. et al.

(10) Patent No.: US 11,879,905 B2
(45) Date of Patent: Jan. 23, 2024

(54) STRAIN SENSOR BASED DOWNHOLE FLUID DENSITY MEASUREMENT TOOL

(71) Applicant: Halliburton Energy Services, Inc., Houston, TX (US)

(72) Inventors: James Dan Vick, Jr., Dallas, TX (US); Michael Linley Fripp, Carrollton, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 201 days.

(21) Appl. No.: 16/954,828

(22) PCT Filed: Sep. 17, 2019

(86) PCT No.: PCT/US2019/051544
§ 371 (c)(1),
(2) Date: Jun. 17, 2020

(87) PCT Pub. No.: WO2021/054943
PCT Pub. Date: Mar. 25, 2021

(65) Prior Publication Data
US 2022/0050036 A1    Feb. 17, 2022

(51) Int. Cl.
*G01N 9/10* (2006.01)
*G01N 33/28* (2006.01)
(Continued)

(52) U.S. Cl.
CPC ............... *G01N 9/10* (2013.01); *E21B 47/01* (2013.01); *E21B 47/10* (2013.01); *G01N 9/18* (2013.01); *G01N 33/2823* (2013.01)

(58) Field of Classification Search
CPC ........ G01N 9/10; G01N 33/2823; G01N 9/18; E21B 47/01; E21B 47/10
See application file for complete search history.

(56) References Cited

U.S. PATENT DOCUMENTS 9,187,984 B2    11/2015    Usadi et al.
9,347,288 B2 *   5/2016    Clemens ................. E21B 44/00
(Continued)

FOREIGN PATENT DOCUMENTS

CN      102926739 A      2/2013
GB        2190500 A  * 11/1987   ............. G01F 23/68
(Continued)

OTHER PUBLICATIONS

PCT Application Serial No. PCT/US2019/051544, International Search Report, dated Jun. 12, 2020, 4 pages.
(Continued)

*Primary Examiner* — Farhana A Hoque
*Assistant Examiner* — Joseph O Nyamogo
(74) *Attorney, Agent, or Firm* — DeLizio, Peacock, Lewin & Guerra, LLP

(57) ABSTRACT

Systems and methods for determining fluid density include receiving calibration data for a fluid density measurement tool. The fluid density measurement tool can include a cantilever beam and at least one strain sensor that is coupled to the cantilever beam. The cantilever beam can be housed in the fluid density measurement tool and is buoyed by a fluid that enters the fluid density measurement tool. The systems and methods measure strain values at the at least one strain sensor and determine a density of the fluid based on the calibration data, and the strain values measured at the at least one strain sensor.

20 Claims, 12 Drawing Sheets

(51) Int. Cl.
*E21B 47/10* (2012.01)
*G01N 9/18* (2006.01)
*E21B 47/01* (2012.01)

(56) References Cited

U.S. PATENT DOCUMENTS

| | | | |
|---|---|---|---|
| 9,708,898 | B2 | 7/2017 | Milner et al. |
| 2002/0178803 | A1 | 12/2002 | Pelletier et al. |
| 2005/0160806 | A1* | 7/2005 | Yoshioka ............ G01F 23/0038 |
| | | | 73/305 |
| 2007/0294039 | A1* | 12/2007 | Gysling .................... G01F 1/74 |
| | | | 702/24 |
| 2008/0223130 | A1 | 9/2008 | Snell et al. |
| 2011/0042070 | A1 | 2/2011 | Hsu et al. |
| 2012/0085161 | A1 | 4/2012 | Kumar |
| 2013/0180330 | A1 | 7/2013 | Gao et al. |
| 2013/0239671 | A1 | 9/2013 | Gisolf et al. |
| 2015/0070000 | A1 | 3/2015 | Gao et al. |
| 2015/0101404 | A1 | 4/2015 | Chen et al. |
| 2015/0184510 | A1 | 7/2015 | Gao et al. |
| 2015/0316461 | A1* | 11/2015 | Dunn ...................... G01N 15/05 |
| | | | 73/61.65 |
| 2016/0320280 | A1* | 11/2016 | Kerr ......................... E21B 49/00 |
| 2017/0270225 | A1* | 9/2017 | Chen ....................... G06F 16/00 |

FOREIGN PATENT DOCUMENTS

| | | |
|---|---|---|
| WO | 2002077613 A2 | 10/2002 |
| WO | 2016043722 A1 | 3/2016 |

OTHER PUBLICATIONS

PCT Application Serial No. PCT/US2019/051544, International Written Opinion, dated Jun. 12, 2020, 6 pages.
"A Revolution in Reservoir Characterization", Middle East Well Evaluation Review, 1996, pp. 43-55.

\* cited by examiner

STRAIN SENSOR BASED DOWNHOLE FLUID DENSITY MEASUREMENT TOOL

TECHNICAL FIELD

The disclosure generally relates to the field of fluid density measurements and more particularly to density measurements of downhole fluids in a borehole.

BACKGROUND

Evaluation of fluids produced from subsurface formal ions or used during drilling wellbores into such formations can be important data that can be used to improve hydrocarbon recovery operations. Such fluids can include drilling fluids, completion fluids production fluids, formation fluids, etc.

Evaluation of such fluids can be dependent on the ambient downhole environment. For example, downhole temperature and pressure can affect evaluation of the fluids. In addition, a state of the fluid can be altered in response to being brought to the surface. For example, a gas can change to liquid, a liquid can change to a solid, etc. Thus, evaluation of such fluids should be performed downhole in order to produce accurate results. However, downhole fluids and high flow rates can damage conventional sensors used to measure fluid density.

BRIEF DESCRIPTION OF THE DRAWINGS

Embodiments of the disclosure may be better understood by referencing the accompanying drawings.

Figure 1A:
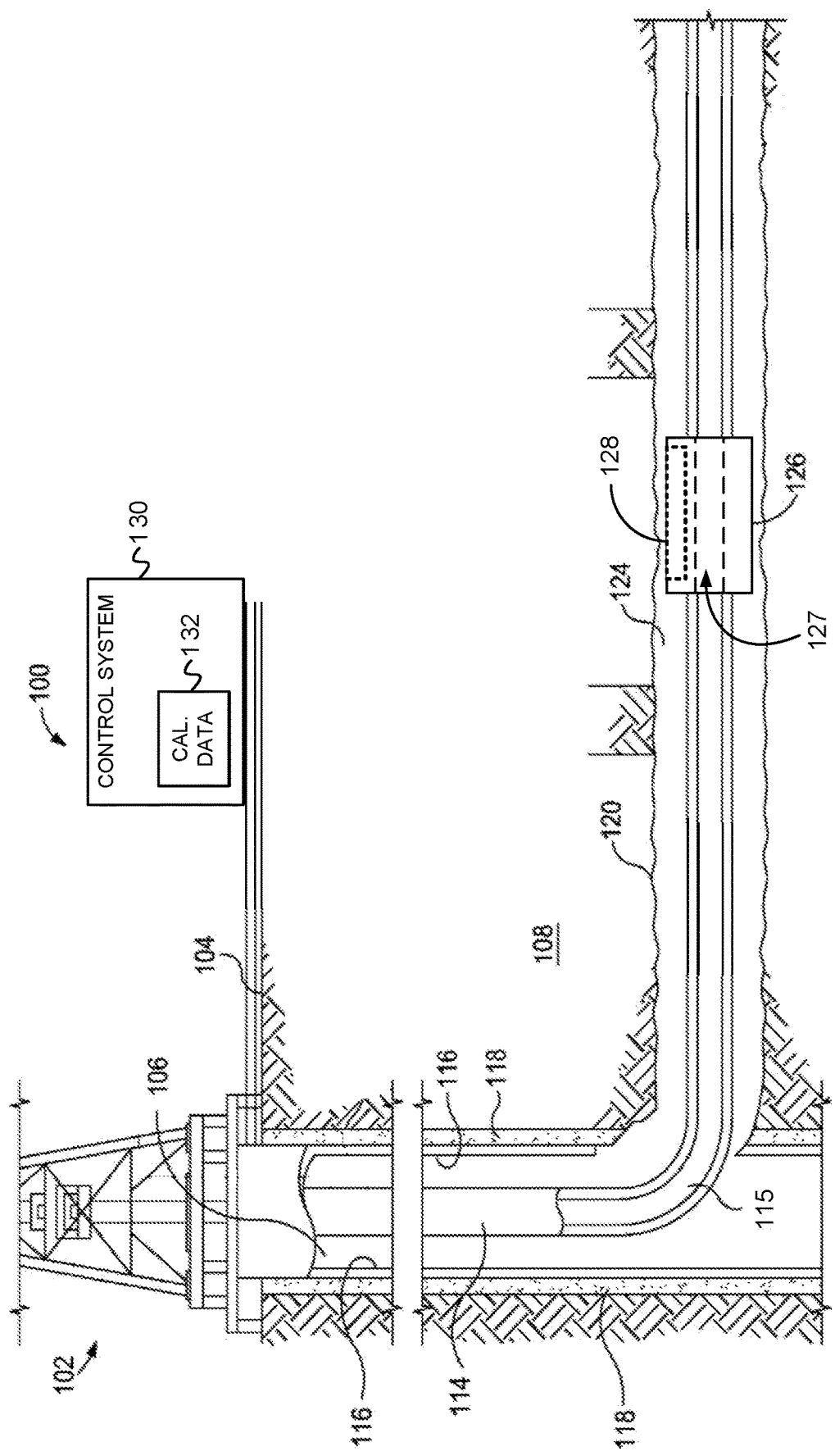
FIG. 1A illustrates an example well system that may employ one or more embodiments of the fluid density measurement tool described herein.

The drawings are provided for the purpose of illustrating example embodiments. The scope of the claims and of the disclosure are not necessarily limited to the systems, apparatus, methods, or techniques, or any arrangements thereof, as illustrated in these figures. In the drawings and description that follow, like parts are typically marked throughout the specification and drawings with the same or coordinated reference numerals. The drawing figures are not necessarily to scale. Like or the same parts illustrated in different figures may not be represented using the same scale or relative proportions between the figures. Certain features of the invention may be shown exaggerated in scale or in somewhat schematic form, and some details of conventional elements may not be shown in the interest of clarity and conciseness.

DETAILED DESCRIPTION

The description that follows includes example systems, methods, techniques, and program flows that embody aspects of the disclosure. However, it is understood that this disclosure may be practiced without these specific details. For instance, this disclosure refers to machine learning for calibration of a fluid density measurement tool in illustrative examples. Embodiments of this disclosure can be used any other type of artificial intelligence for such calibration. In other instances, well-known instruction instances, protocols, stitches and techniques have not been shown in detail in order not to obfuscate the description.

Various embodiments include a downhole fluid density measurement tool in which one or more sensors included as part of the measurement tool are configured to measure a density and/or a temperature of a fluid in a downhole environment, wherein the one or more sensors are not directly exposed to the well fluid, thereby increasing the life of the sensors. In some embodiments, a tool to measure fluid density downhole includes one or more strain sensors or gauges attached to a cantilever beam. The measured strain changes when the cantilever beam is placed in a fluid due to buoyancy of the cantilever beam in the fluid. A density of the fluid can be determined based on the strain measured by the strain sensors or gauges. In various embodiments, the one or more sensors may be configured to determine a temperature of fluids in a downhole environment with or without also being configured to determine densities of the fluids.

The downhole fluid density measurement tool can include a density stick (that includes a cantilever beam with strain sensors or gauges) and a tubing housing. The strain sensors or gauges can be located in a protected section of the fluid density measurement tool. Some embodiments determine a fluid density without using measured properties, such as an outer or inner diameter of the protected section that encloses the strain sensors or gauges.

The downhole fluid density measurement tool can be calibrated at the surface before being deployed downhole. In some embodiments, calibration includes creating a machine learning model. The machine learning model can be created based on fluids at different densities and temperatures, wherein the tool is put through a series of gyrations (e.g., tilts, rotations, etc.). Additionally, the machine learning model can be updated in the wellbore after properties in the wellbore are known. For example, a completion fluid with known properties can be used to enhance the machine learning model before the well is operational with fluids having unknown properties. Additionally, because various embodiments use a machine learning model, the required number of strain sensors or gauges needed to accurately measure fluid density can be reduced (e.g., from three to two). For example, a fluid density measuring tool can include three strain sensors or gauges; however, only two of the strain sensors or gauges may be necessary in some situations. In some embodiments, a single strain sensor or gauge may be used to determine density and/or temperature measurements of a fluid in a downhole environment. Use of the machine learning model as described herein allows the fluid density measurement tool to continue to accurately measure fluid density even for example when one or some number less than the total number of a plurality of strain sensors or gauges included in a measurement tool fail.

FIG. 1A illustrates au example well system 100 that may employ one or more embodiments of the downhole monitoring tool described herein. As illustrated, the well system 100 may include wellhead equipment 102 arranged at the Earth's surface 104 and a wellbore 106 extending therefrom and penetrating, a subterranean formation 108. The wellhead equipment 102 may encompass a drilling rig, a wellhead installation, a Christmas tree, a work-over rig, a service rig, etc. It should be noted that, even though FIG. 1A depicts a land-based well system 100, it will be appreciated that the embodiments disclosed herein are equally well suited for use in any other type of rig including, but not limited to, floating or sea-based platforms and rigs, or rigs used in any other geographical location without departing from the scope of the disclosure.

In some embodiments, the wellhead equipment 102 may be an oil and gas rig configured to stimulate and otherwise prepare a wellbore 106 and surrounding subterranean formation 108 for the production of hydrocarbons therefrom. In some embodiments, a fluid such as a stimulation fluid (e.g., water with additives) may be provided through wellbore tubular 114. In other embodiments, the wellhead equipment 102 may be a wellhead assembly configured for the production of hydrocarbons from the wellbore 106. In some embodiments, a fluid such as gas and/or other hydrocarbon fluids may be extracted from wellbore 106 via wellbore tubular 114 and a thus passageway 115 included within wellbore tubular 114.

The wellhead equipment 102 may support or otherwise help manipulate the axial position of the wellbore tubular 114 as extended into the wellbore 106. In some embodiments, the wellbore tubular 114 may include, but not be limited to, one or more types of connected lengths of drill string, casing string, production tubing, landing string, liners, coiled tubing, combinations thereof, and the like. As illustrated in FIG. 1A, the wellbore 106 may extend substantially vertically away from the surface 104 over a vertical wellbore portion. In other embodiments, the wellbore 106 may otherwise deviate at any angle from the surface 104 over a deviated or horizontal wellbore portion. In some embodiments, portions or substantially all of the wellbore 106 may be vertical, deviated, horizontal, and/or curved.

In an embodiment, the wellbore 106 may be at least partially cased with a casing string 116 or may otherwise remain at least partially or wholly uncased. The casing string 116 may be secured in position within the wellbore 106 using, for example, cement 118. In other embodiments, the casing string 116 may be only partially cemented within the wellbore 106 or, alternatively, may be entirely uncemented. A lower portion of wellbore tubular 114 may extend into a branch or lateral portion 120 of the wellbore 106. As illustrated, the lateral portion 120 may be an uncased or "open hole" section 124 of the wellbore 106. In some embodiments, the entirety of the wellbore 106 is uncased. In other embodiments, lateral portion 120 represents a completed and production wellbore, wherein wellbore 114 extends through section 124, and section 124 represents a cased portion of the wellbore 106.

The well system 100 may further include a fluid density measurement tool 126 arranged in, coupled to, or otherwise forming an integral part of the wellbore tubular 114. Measurement tool 126 in various embodiments includes a thru passageway 127 couple to thru passageway 115 of wellborn tubular 114, and configured to allow fluids being transported along passageway 115 to also be transported thru passageway 127. Measurement tool 126 in various embodiment also includes a density stick 128 that includes one or more sensors or gauges, such as one or more strain sensors. Measurement tool 126 may be configured so that one or more first portions of the density stick are exposed to a fluid, such as a stimulation or a production fluid, that is being transported thru or is present within passageway 127, and wherein one or more second portions of the density stick, including the one or more sensors or gauges, are protected from exposure to the fluid being transported thru or that is present within passageway 127. Various embodiments of measurement tool 126 that may be included in a well system 100 are further illustrated and described below with respect to FIGS. 3-8.

While only one fluid density measurement tool 126 is depicted in FIG. 1A, in various embodiments more than one fluid density measurement tool 126 may be used without departing from the scope of the disclosure. Further, while the fluid density measurement tool 126 is depicted in FIG. 1A as being in a horizontal portion of the wellbore tubular 114, embodiments of a fluid density measurement tool 126 may be positioned in a vertical portion of the wellbore tubular 114, or at a position of the wellbore tubular 114 that is between horizontal and vertical. Moreover, the fluid density measurement tool 126 may be arranged in any configuration desired to fit a particular application.

Measurement data from the fluid density measurement tool may be communicated to a control system 130. The control system 130 can be communicably coupled to the fluid density measurement tool 126 to receive data from the fluid density measurement tool 126. The control system 130 can be communicably coupled to the fluid density measurement tool 126 via a wired communication link or a wireless communication link (e.g., radio wave, mud pulse telemetry etc.). Further, the control system 130 can receive calibration data 132. The control system 130 can include processor and memory resources (e.g. comprising computer system 1100, FIG. 11), which can control various aspects of the operation of the well system 100. For example, the control system can receive data from the fluid density measurement tool 126 and use the calibration data 132 to correlate the received data to a density of a fluid flowing through the wellbore annular 114. The control system 130 can then control other devices in the wellbore system 100 based on the fluid density. For example, the control system 130 can control a downhole choke based on the fluid density determined by the control system using measurements provided by the fluid density measurement tool 126. Although shown as being at the surface, the control system 132 can be located anywhere either above or below the surface. Further, the control system 132 may control a single downhole device or a group of downhole devices.

FIG. 1A shows an embodiment having a single fluid density measurement tool 126. The fluid density measurement tool 126 provides a localized measurement of the fluid density at the location of the tool. In alternative embodiments, multiple fluid density measurement tools 126 can be distributed along a wellbore tubular. The different fluid density measurement tools 126 can be at different axial locations along the wellborn tubular. Positioning the fluid density measurement tools at different axial locations along tire wellbore tubular can help identify the locations along the wellborn tubular where different densities of fluid are entering. The different fluid density measurement tools 126 can also be at different circumferential locations around the wellborn tubular. Positioning she fluid density measurement tools at different circumferential locations around the wellbore tubular can help identify multiple phases of fluid where the gas might float on the oil that might float on the water. The multiple fluid density tools 126 can provide multiple localized measurements or used to detect changes in density. Further, the measurements from the multiple tools can be averaged or otherwise combined to determine a bulk or average density for a fluid in the wellbore.

It is noted that the use of directional terms, such as above, below, upper, lower, upward, downward uphole, downhole, and the like are used in relation to the illustrative embodiments as they are depicted in the figures herein, the upward direction being toward the top of the corresponding figure and the downward direction being toward the bottom of she corresponding figure, the uphole direction being toward the surface of the well and the downhole direction being toward the top or bottom of the well.

Figure 1B:
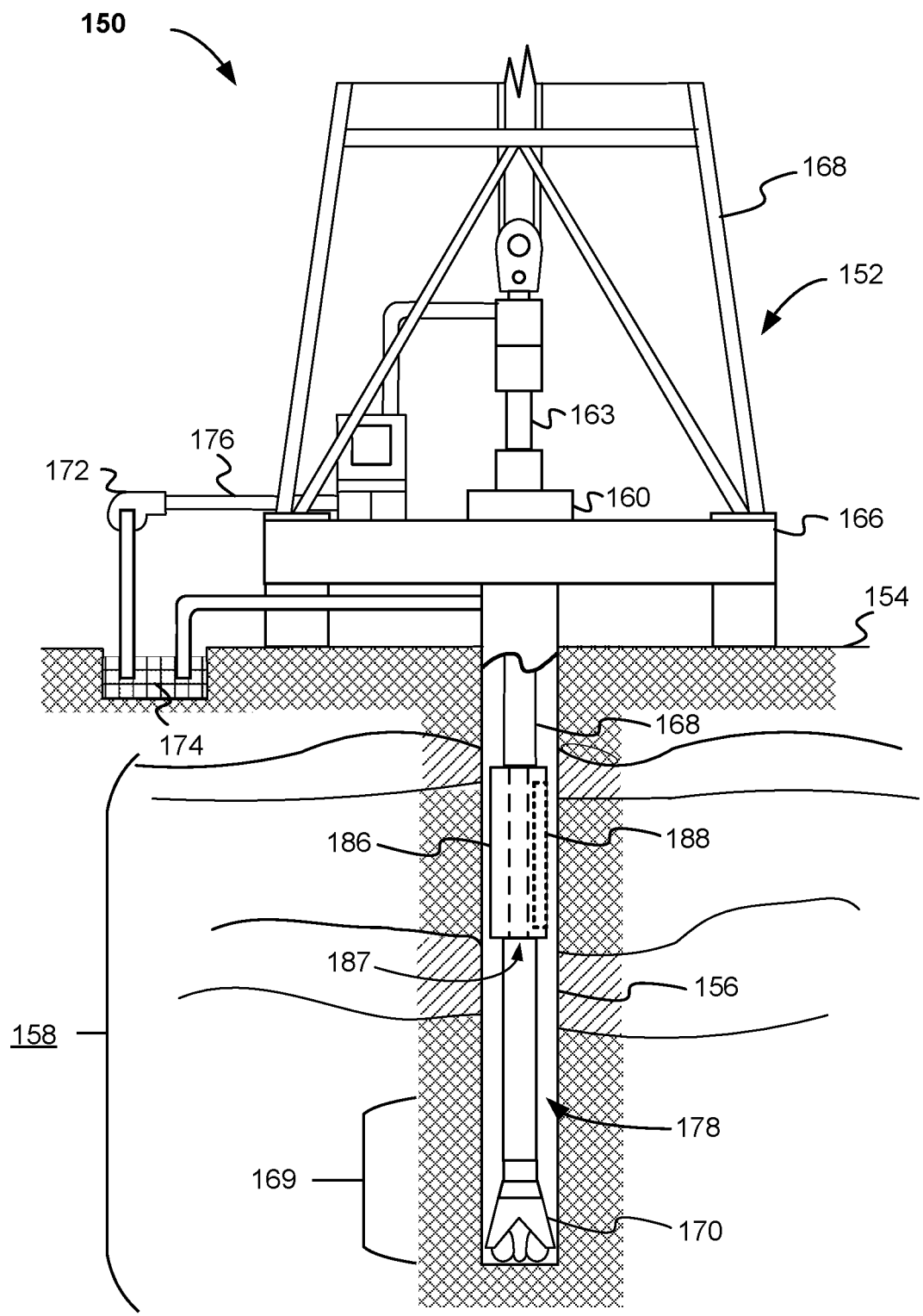
FIG. 1B illustrates an example well system that may employ one or more embodiments of the fluid density measurement tool described herein.

FIG. 1B illustrates an example well system 150 that may employ one or more embodiments of the downhole monitoring tool described herein. As illustrated, the well system 150 may include wellhead equipment 152 arranged at the Earth's surface 154 and a borehole 156 extending therefrom and penetrating a subterranean formation 158. The wellhead equipment 152 may encompass a drilling rig as further described below. It should be noted that, even though FIG. 1B depicts a land-based well system 150, it will be appreciated that the embodiments disclosed herein are equally well suited for use in any other type of rig including, but not limited to, floating or sea-based platforms and rigs, or rigs used in any other geographical location without departing from the scope of the disclosure.

In various embodiments of system 150, drilling of oil and gas wells is carried out using a string of drill pipes connected together so as to form a drilling string 168 that is lowered through a rotary table 160 into borehole 156. A drilling platform 166 positioned on surface 154 is equipped with a derrick 168 that supports a hoist 167. The derrick 168 and hoist 167 are configured to provide support for the drill string 168. The drill string 168 is configured to penetrate the rotary table 160 and in some embodiments to be rotated to perform further drilling operations on borehole 156 through subsurface formations 158. The drill string 168 may include a Kelly 163, and one or more drill pipes coupled to a bottom hole assembly (BHA) 169, including a drill bit 170 located at the loner portion of the drill string. The BHA 169 may include drill collars, one or more downhole tools, such as log-while drilling (LWD) tools, measurement-while-drilling (MWD) tools, and/or other sensors in addition to drill bit 170.

During drilling operations that are being performed by system 150, the drill string 168 (including the Kelly 163, the drill pipes and the bottom hole assembly 169) may be rotated by the rotary table 160. In addition to, or alternatively, the bottom hole assembly 160 may be rotated by a motor (not shown in FIG. 1B, but e.g., a mud motor) that is located downhole. The drill collars and/or drill pipes included in drill string 168 may be used to add weight to the drill bit 170. The drill collars may also operate to stiffen the bottom hole assembly 169, allowing the bottom hole assembly 169 to transfer the added weight to the drill but 170, and in turn, to assist the drill bit 170 in penetrating the subsurface formation and extend borehole 156.

As part of a drilling operation being performed by system 150, a mud pump 172 may pump drilling fluid (sometimes referred to as "drilling mud") from a mud pit 174 through a hose 176 into the drill string 168 and down to the drill bit 170. The drilling fluid can flow out from the drill bit 170 and be returned to the surface 154 through an annulus area 178 between the drill string 168 and the sides of borehole 156. The drilling fluid may then be returned to the mud pit 174, where such fluid is filtered. In some embodiments, the drilling fluid can be used to cool the drill bit 170, as well as to provide lubrication for the drill bit 170 during drilling operations. Additionally, the drilling fluid may be used to remove cuttings of subsurface formation 158 created by operating the drill bit 170 in the process of extending borehole 156 further into the subsurface formation 158. In various examples, determining a density or a change in density of the drilling fluid is an important parameter associated with the drilling operation. In addition, determining temperature and/or changes in temperature of the drilling fluid may also be an important parameter associated with the drilling operation.

As illustrated in FIG. 1B, a fluid density measurement tool 186 may be positioned somewhere downhole in borehole 156, and be configured to provide density and/or temperature measurements associated with fluids, such as drilling fluid, being transported thru and/or that are present in the borehole 156. In some embodiments, measurement tool 186 includes a thru passageway 187 that is in fluid communication with the passageway extending through drill string 168 so that drilling fluid passing through or present within the drill string will also pass through or be present in the passageway 187. A density stick 188 tint includes one or more sensors 188 may be included as part of measurement tool 186 and configured to provide output signals that may be processed to determine density values and/or temperature values for the fluid passing through or present in passageway 187. As such, measurement tool 186 may be configured in various embodiments to provide measurements representative of density values and/or temperature values for fluid, such as drilling fluid, that is being transported from surface 154 down through the drill string 168 to drill bit 170.

In addition to or in the alternative, in various embodiments measurement tool 186 may be positioned within borehole 156 and outside of drill string 168 so that a fluid, such as drilling fluid that has exited the drill string and is flowing back toward surface 154 thru area 178 is received, at least in part, at measurement tool, 186. Measurement tool 188 may be configured in various embodiments to provide measurement representative of density values and/or temperature values for this fluid, such as drilling fluid, that is being transported toward surface 154 through area 178.

Various embodiments of measurement tool 186 that may be included in a well system 150 are further illustrated and described below with respect to FIGS. 3-8. And while only one fluid density measurement tool 186 is depicted in FIG. 1B, in various embodiments more than one fluid density measurement tool 186 may be used without departing front the scope of the disclosure. For example, a plurality of measurement tools 186 may be deployed along different positions of the drill string, 168, and/or at one or more positions within borehole 156 but outside of the drill string. Further, while the fluid density measurement tool 186 is depicted in FIG. 1B as being in a vertical portion of the borehole 156, embodiments of a fluid density measurement tool 186 may be positioned in a horizontal portion of the borehole and have a horizontal orientation, or at a position of a borehole and having an orientation that is anywhere between horizontal and vertical. Moreover, the fluid density measurement tool 186 may be arranged in any configuration desired to fit a particular application.

Measurement data from the fluid density measurement tool 168 may be communicated to a control system (not shown in FIG. 1B, but for example a control system such as control system 130 as illustrated and described with respect to FIG. 1A). The control system may be communicable coupled to the fluid density measurement tool 186 to receive data from the fluid density measurement tool 186, for example via a wired communication link or a wireless communication link (e.g., radio wave, mud pulse telemetry etc.). Further, the control system may receive calibration data, and may include processor and memory resources (e.g. comprising computer system 1100, FIG. 11), which can control various aspects of the operation of the well system 150 in a same or similar manner as described above with respect to system tool of FIG. 1A. Various embodiments of the measurement tools described herein may be configured to measure fluid density downhole based on a cantilever beam and strain sensors or gauges.

Figure 2:
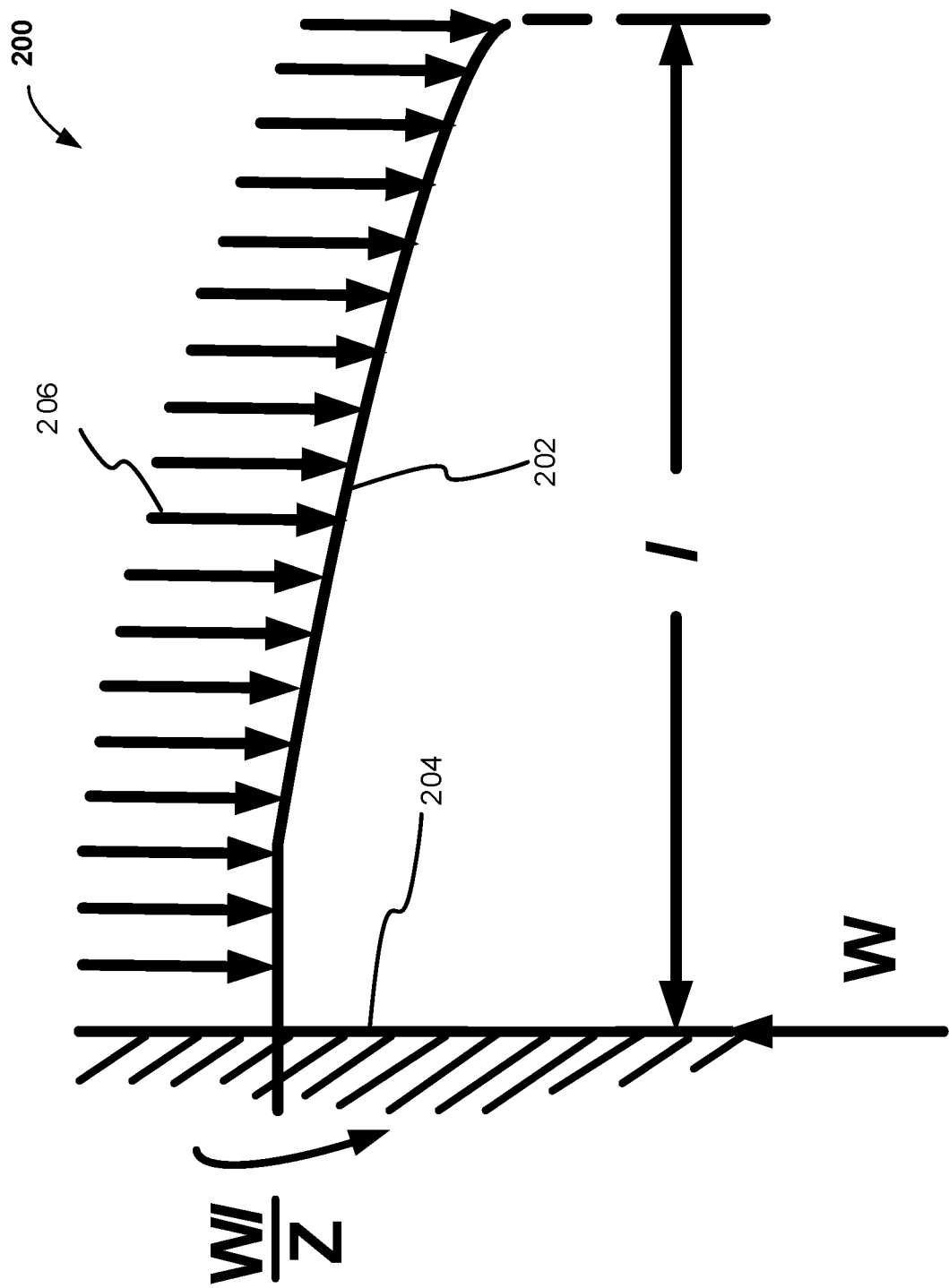
FIG. 2 depicts a graph showing how measured strain changes when a cantilever beam is placed in a fluid due to buoyancy.

FIG. 2 depicts a graph 200 showing how measured strain changes due to buoyancy when a cantilever beam is placed in a fluid. The graph 200 includes a cantilever beam 202 attached to a wall 204 having forces 206 distributed across the cantilever beam 202 that are applied downward causing the cantilever beam 202 to bend. The cantilever beam 202 has a length l. The forces 206 apply a total weight W across the cantilever beam 202. W is thus related to the buoyancy of the cantilever beam in the fluid being measured. Z is the moment of inertia of the beam. The stiffness of the beam can be determined based on Z, the shape of the beam and material of the beam. The term Wl/Z is the stress in the beam at the outside edge of the beam (l) to the wall 204. That stress can be measured by the strain sensor or gauge (hereinafter sensor) and the measurements can be used as described below to determine a fluid density.

Figure 3:
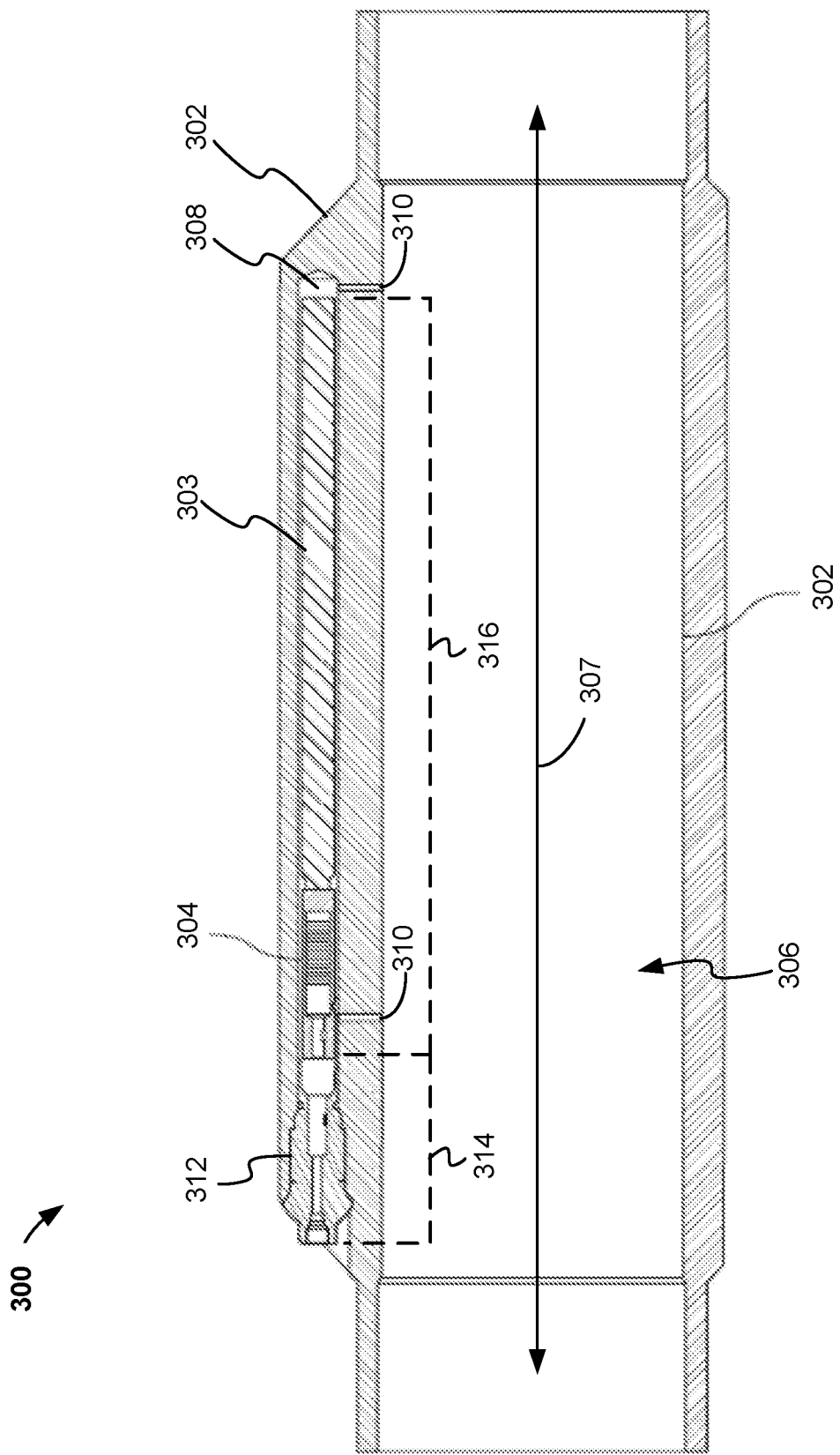
FIG. 3 depicts a cross-sectional view of a fluid density measurement tool according to some embodiments.

FIG. 3 depicts a cross-sectional view of a fluid density measurement tool 300, according to some embodiments. Measurement tool 300 may be an embodiment of measurement tool 126 as described and illustrated with respect to FIG. 1A, and/or measurement tool 186 as described and illustrated with respect to FIG. 1B. Referring back to FIG. 3, in some embodiments, the fluid density measurement tool 300 has a housing 302 (shown in cutaway in FIG. 3) at least partially enclosing a tubular area 306 positioned within the housing. Well fluid or other fluids may flow in or through the tubular area 306 as generally indicated by arrow 307. A density stick 304 may be inserted into a chamber formed by a hollow area 308 of the housing 302. In various embodiments the density stick 304 new be fixed to the housing 302 at portion 314 of the hollow area 308 and is suspended within portion 316 of the hollow area 308. Density stick 304 may include a rod 303 (shown in cutaway in FIG. 3) that is coupled to other components of the density stick, and extends into at least some portion of hollow area 308. Openings 310 allow fluid (e.g., well fluid) from tubular area 306 to flow into the hollow area 308. Portions of the density stick 304, including rod 303, are buoyed by the fluid in hollow area 308 while not touching, the housing area 302 of the fluid density measurement tool 300. The pap between the density stick 304 and the inside wall of the housing in hollow area 308 allows for a droop of the portions of the density stick that new be buoyed by a fluid present in the hollow area 308. The amount of droop may be a function of the density, among other factors such as the weight of rod 303 and the orientation (horizontal, vertical, other) of the density stick 304.

In some embodiments, the maximum anticipated droop of the buoyed portion of the density stick 304 may be as little as 0.001 to 0.002 inches (0.00254 to 0.00508 cm). In some embodiments, the anticipated amount of droop of the density stick may include a range of values extending from of zero to 0.250 inches (0.00 to 0.635 cm) inclusive. In some embodiments, the density stick may be threaded into the housing at thread location 312. Locating density stick 304 in the hollow area 308 can be desirable because it can protect the density stick from the high flow rates that may be present as fluid flows though the tubular area 306. The density stick 304 is depicted as a cylinder, which can allow fin averaging, the density across the entire flow area. While depicted as a cylinder, the density stick 304 can be other types of shapes. For example, the density stick 304 can include multiple cross-sections including polygonal (e.g., square) and curved (e.g., round, kidney bean, and ovular). Additionally, the cross-section does me need to be consistent along the length and vary in area and shape. In some embodiments, the density stick 306 is a cylinder that goes partially around or completely around the circumference of the tubing (wherein the portion 316 revolves around the centerline).

Figure 4:
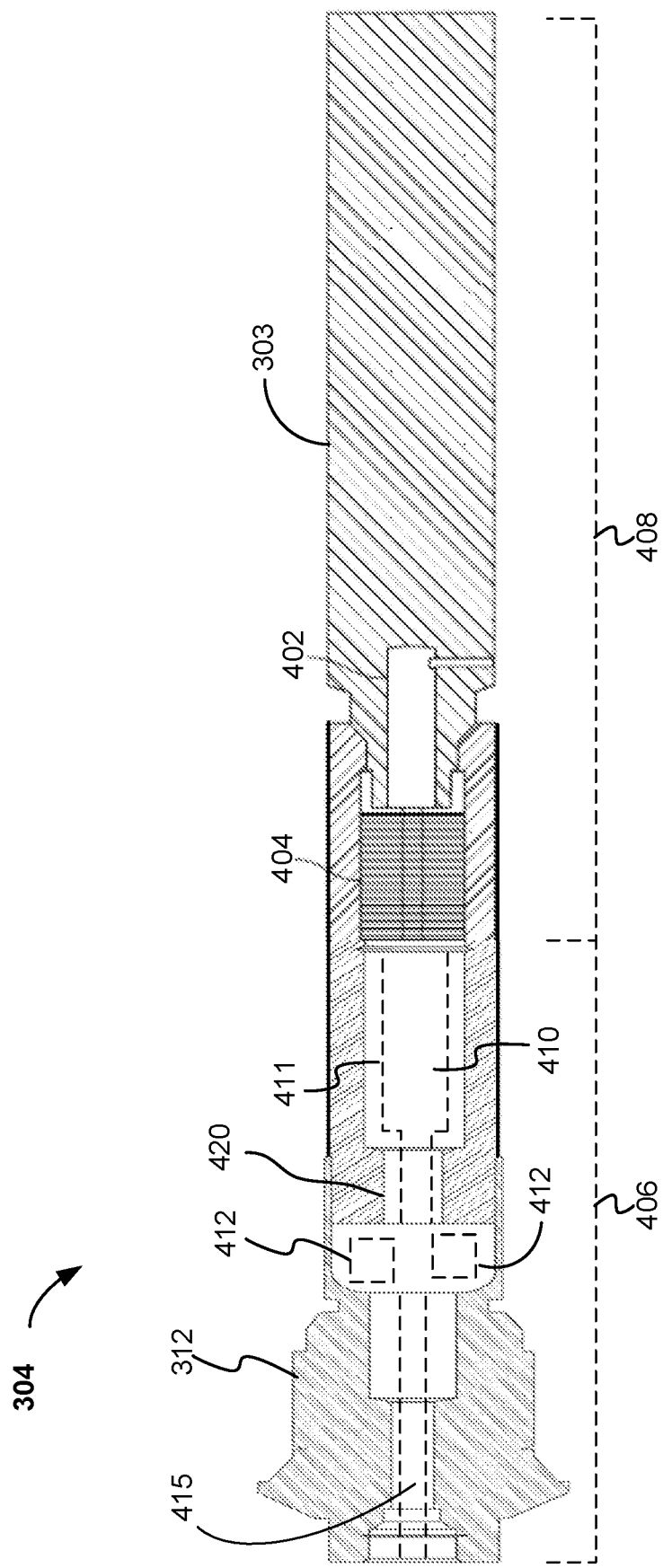
FIG. 4 depicts a cross-sectional view of a density measurement stick in a fluid density measurement tool, according to some embodiments.

FIG. 4 depicts a cross-sectional view of a density measurement stick 304 in a fluid density measurement tool according to some embodiments. FIG. 4 depicts further details of density stick 304 that may be included in a fluid density measurement tool such as measurement tool 300 as illustrated and described above with respect to FIG. 3. For purposes of discussion below, the density stick 304 as illustrated in FIG. 4 is divided into a left portion 406 and a right portion 408. Density stick 304 includes threaded location 312 at a first end portion (left portion 406) of the density stick, and rod 303 at a second end portion (right portion 408) of the density stick. In various embodiments, left portion 406 includes a passageway 415 extending from an opening at the far end of left portion 406, through sensor housing 414, and thru to coupling 411. Coupling 411 may be coupled to sensor housing 414 through connector 420. Coupling 411 includes a hollow chamber 410. In some embodiments, the right portion 408 of density stick 304 comprises a circular beam having a bellows 404, and a fluid chamber 402 extending through a portion of rod 303 and in fluid communication with an interior chamber formed by the bellow. It should be noted that the fluid density measurement tool 300 can be oriented in any position. For example, instead of being in horizontal orientation as shown in FIGS. 3-7, the fluid density measurement tool 126 and density stick 304 or portions thereof as illustrated in the figures could be in a vertical orientation, or any orientation between horizontal and vertical. Thus, the designations "left" and "right" as used herein are solely for purposes of describing the embodiments of the density stick, and are not meant to imply any particular operational position of the fluid density measurement tool.

Figure 5:
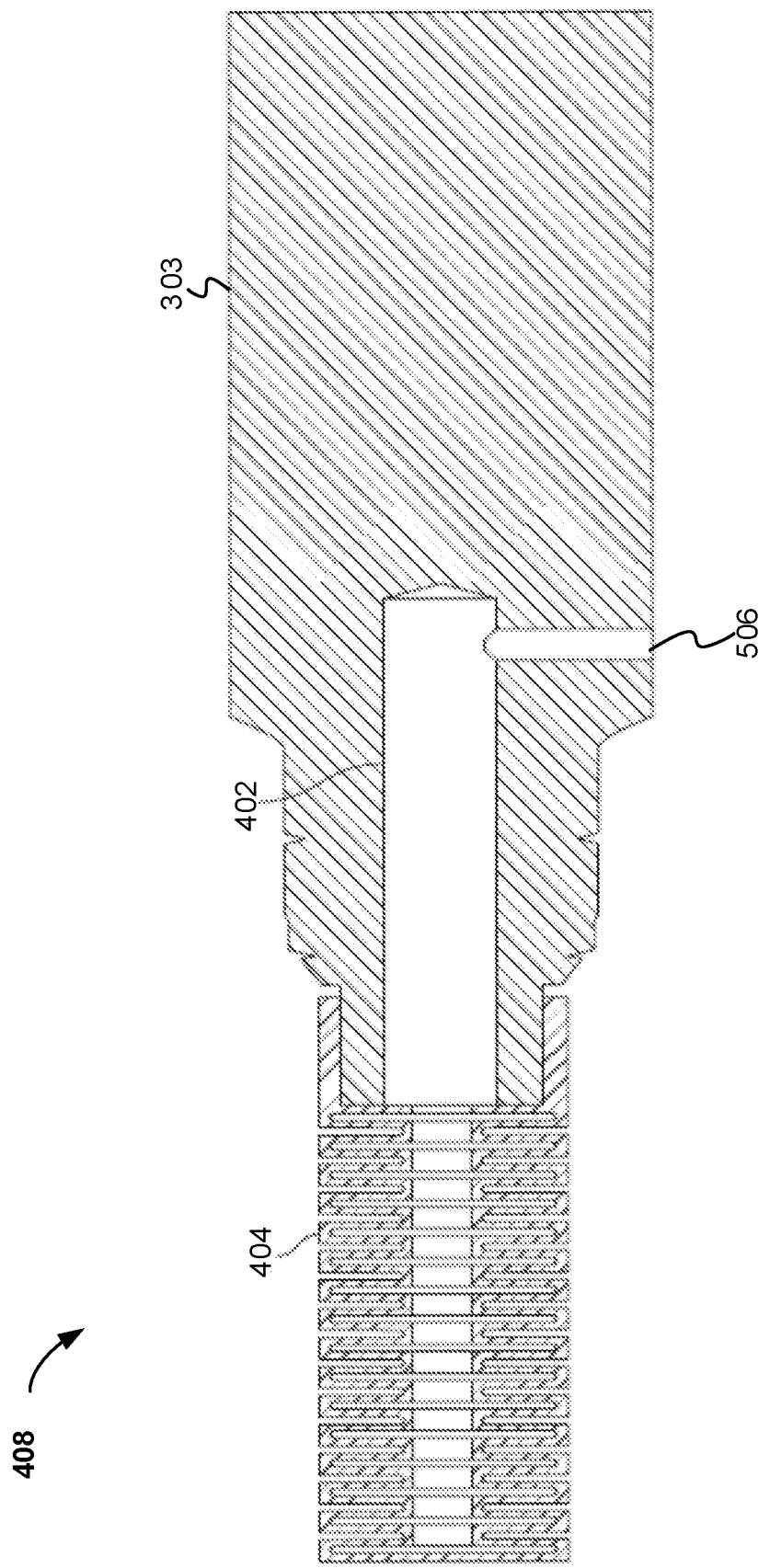
FIG. 5 depicts a more detailed diagram of right portion of a density stick, according to some embodiments.

FIG. 5 depicts a more detailed diagram of the right portion 408 of the density stick 304, according to some embodiments. In some embodiments, the right portion 408 of the density stick includes a weighted rod 303 coupled to the bellows 404. The weighted rod 303 can include the fluid clamber 402. An opening 506 in the weighted rod 303 extends between fluid chamber 402 and area exterior to rod 303, and therefore allows fluid (e.g., well fluid, production fluid) that may be provided in cavity 308 (FIG. 3) to flow into the fluid chamber 402. The bellows 404 can be attached to the weighted rod 303. For example, the bellows 404 can be welded, soldered or otherwise attached to the end of the weighted rod 303. Fluid that is received within fluid chamber 402 may also be received within the interior area of bellows 404, but is sealed within the bellows.

Figure 6:
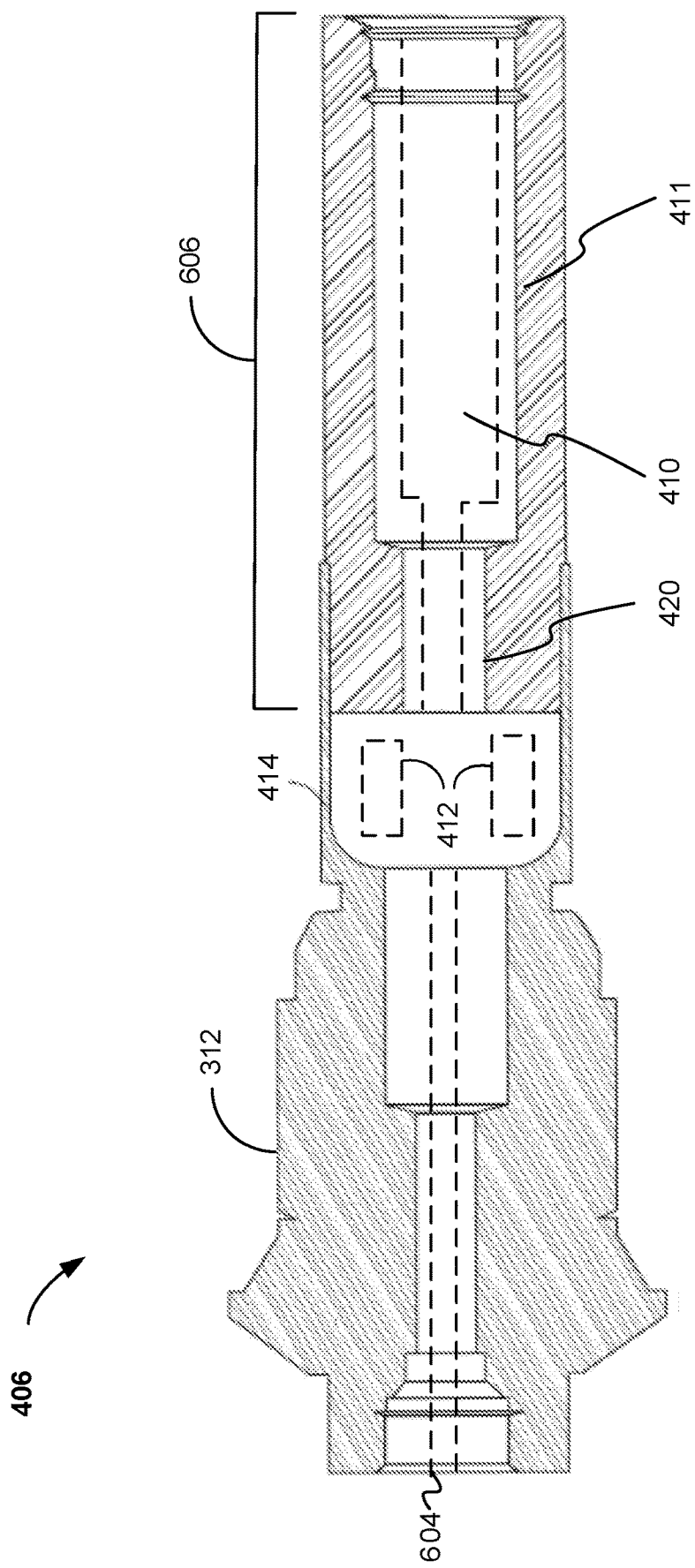
FIG. 6 depicts a more detailed diagram of a left portion of a density stick, according to some embodiments.

FIG. 6 depicts a more detailed diagram of the left portion 406 of the density stick 304, according to some embodiments. The left portion 406 of the density slick 304 includes a thin wall section forming sensor housing 414 where the strain sensors 412 can be located. The strain sensors can be located within the interior of the pipe formed by walls of the left portion 406 of the density stick (including section 414) and are thus protected from the fluid (e.g., well fluid) that surrounds the density stick in the second hollow area 308. Wiring (not shown) coupled to the strain sensors can be used to couple the strain sensors to a measurement system or a control system (such as control system 130, FIG. 1, computer system 1100, FIG. 11). In some embodiments, the interior of left portion 406 of the density stick 304 can include a dielectric fluid bath that can surround and protect the strain sensors and wiring. The wiring can exit the density stick via an opening 604 that is otherwise scaled to prevent the dielectric fluid from escaping and well fluid from entering the interior of the pipe formed within the left portion 406 of the density stick 304. The dielectric fluid can flow into clamber 410 of coupling 411 and surround the outside portion of bellows 404 that has been received within chamber 410. Changes in temperature can cause changes in the volume of the dielectric fluid. The bellows 404 can compensate for the changes in volume, thus preventing buildups of pressure at high temperatures that could cause a rupture in a wall of the tool housing. The weighted rod 303 and bellows 404 including right portion 408 as illustrated in FIG. 5 can be attached to the sensor housing 414 via the coupling 410 and connector 420 as generally indicated by bracket 606.

Figure 7:
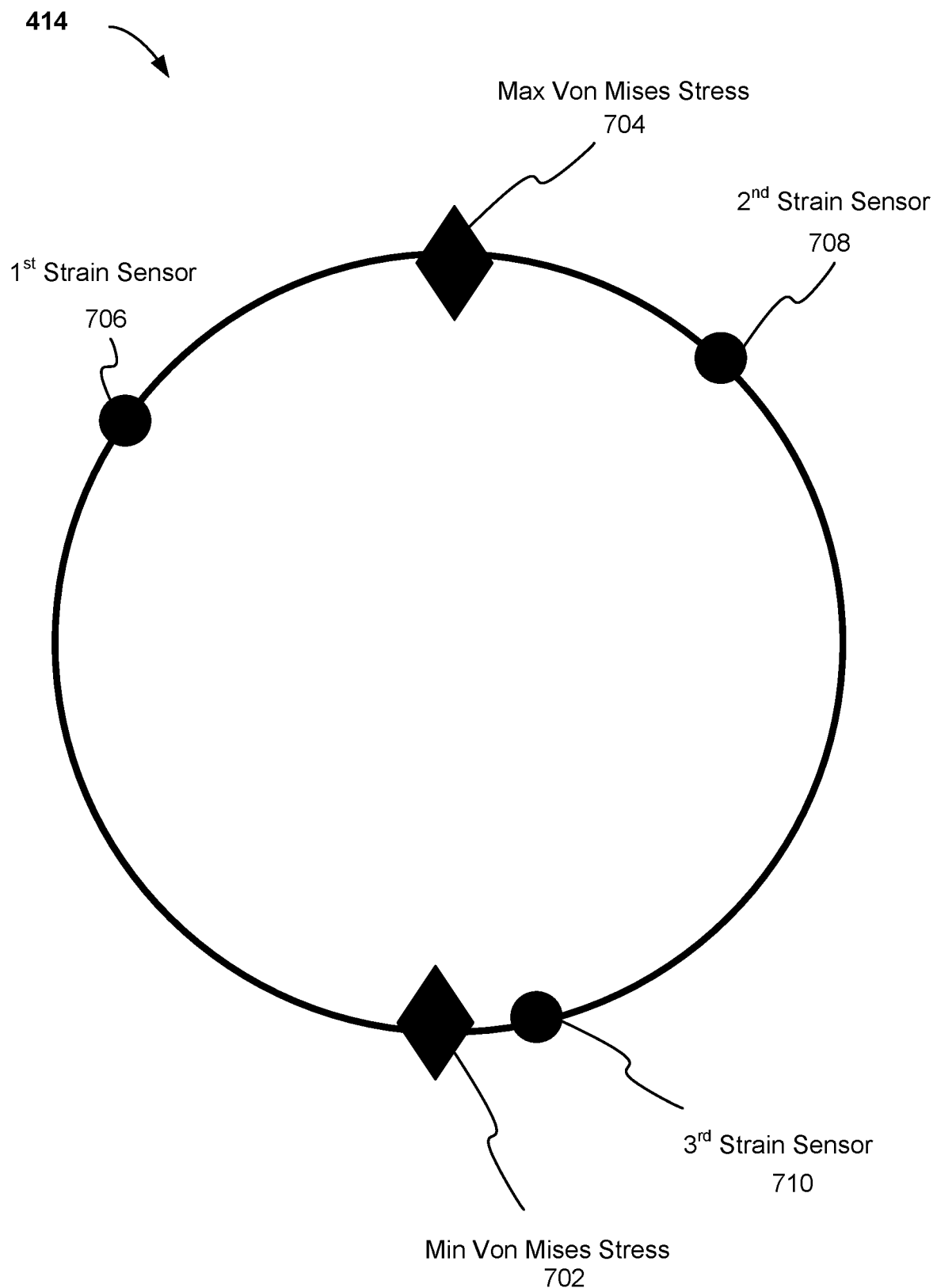
FIG. 7 depicts a schematic representation of the fluid density measurement tool at the thin wall section of lire sensor housing according to various embodiments.

FIG. 7 depicts a schematic representation of the fluid density measurement tool at the thin wall section of the sensor housing 414 according to various embodiments. In some embodiments, one or more strain sensors (three strain sensors 706, 708, 710 are depicted) are positioned in the thin wall section of the sensor housing 414. Although three strain sensors are depicted, fewer or more than three strain sensors can be used. For example, embodiments of sensor housing 414 may include only two sensor. Other embodiments of sensor housing 414 may include four sensors, five sensor, six sensors, or more than six sensors. As further illustrated and described below with respect to FIG. 8, various embodiment of the fluid density measurement tool may include one or more individual sensor, wherein each sensor is located in a separate sensor housing.

Referring again to FIG. 7, in embodiments having three strain sensors, the strain sensors can be positioned 120 degrees apart around the circumference of the sensor housing 414 relative to one another. However, equidistant rotational spacing between the sensors is not required, and in various embodiments the sensors may or may not be rotationally spaced equally relative to one another. In embodiments that have a number of sensors other than three sensor, the sensors may or may not be rotationally spaced equally relative to one another within the sensor housing 414. For example, in a dielectric stick including a sensor housing with two sensors the sensor may be spaced apart from one another by 180 degrees, wherein in alternative embodiments the two sensor may be separated rotationally by some amount other than 180 degrees. Similarly, embodiment of sensor housing 414 that include a number of sensor greater than three may include sensors that are equally spaced rotationally relative to one another, or in the alternative have one or more spacing between sensor that is different for other spacings provided between the sensor.

The measurement values from the strain sensors can be used to calculate a maximum Von Mises stress point 704 and a minimum Von Mises stress point 702. The maximum Von Mises stress point 704 and minimum Von Mises stress point 702 are shown in a vertical position in the example illustrated in FIG. 7. However, the Von Mises stress points may occur at other positions. The maximum and minimum Von Mises stress values can be used to calibrate the fluid density tool 126 and to use the fluid density tool 126 to determine well fluid density as further described below with respect to FIGS. 9 and 10.

The orientation of the strain sensors with respect to the Von Mises stress points 702 and 704 may be different than the example shown in FIG. 7 due to rotation or tilt of the fluid density measurement tool 126. It should be noted that the maximum and minimum Von Mises stress values can be determined regardless of the location of the strain sensors with respect to the locations of maximum and minimum Von Mises stress.

Figure 8:
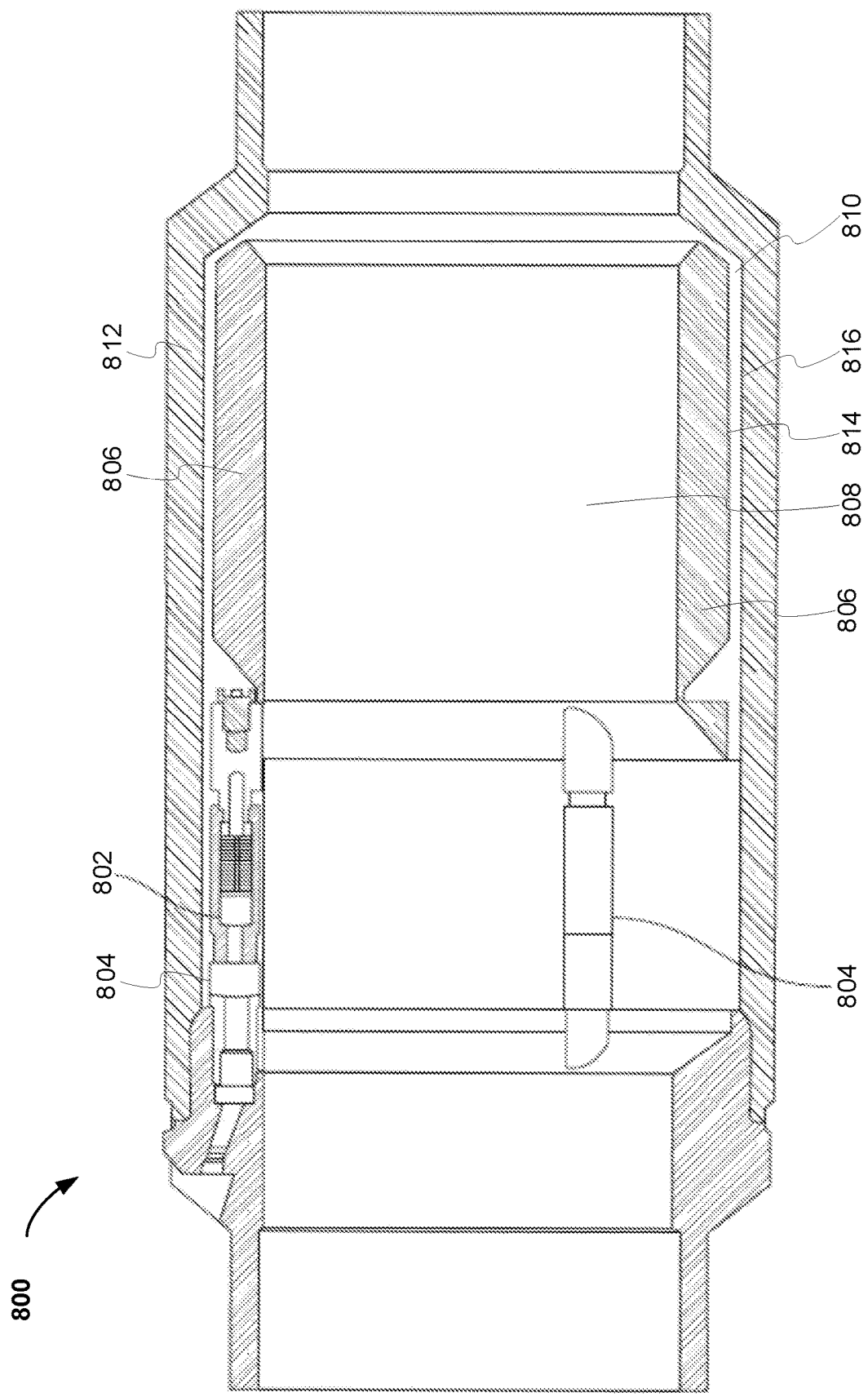
FIG. 8 depicts a cross-sectional view of an alternative fluid density measurement tool according to embodiments.

FIG. 8 depicts a cross-sectional view of an alternative fluid density measurement tool 800 according to one or more embodiments, wherein a weighted tail 806 is used instead of a density stick. Measurement too. 800 includes a housing 812 coupled to a supporting weighted tail 806. The weighted tail 806 comprises tubular cylinder. Multiple strain sensor legs 804 are disposed around the outside portion of the weighted tail 806. In some embodiments, three strain sensor legs 804 are disposed around the weighted tail 806 spaced at 120 degree angles. Each strain sensor leg 804 can include a strain sensor disposed within location 802 of the strain sensor leg 804. The tubular cylinder allows well fluids to flow through the inside portion 808 of the tubular cylinder 806. Additionally, well fluid can flow in a gap 810 formed between the outside wall 814 of the tubular cylinder and the inside wall 816 of the tool 800 housing. Thus, the weighted tail 806 floats the well fluid while allowing well fluid to pass through the tool 800. The strain sensors in strain sensor legs 804 can provide measurements that can be used to determine the minimum and maximum Von Mises stress locations associated with the weighted tail 806. This data can then be used to calibrate the tool 800 and to use the tool 800 to determine well fluid density as further described below with respect to FIGS. 9 and 10.

Figure 9:
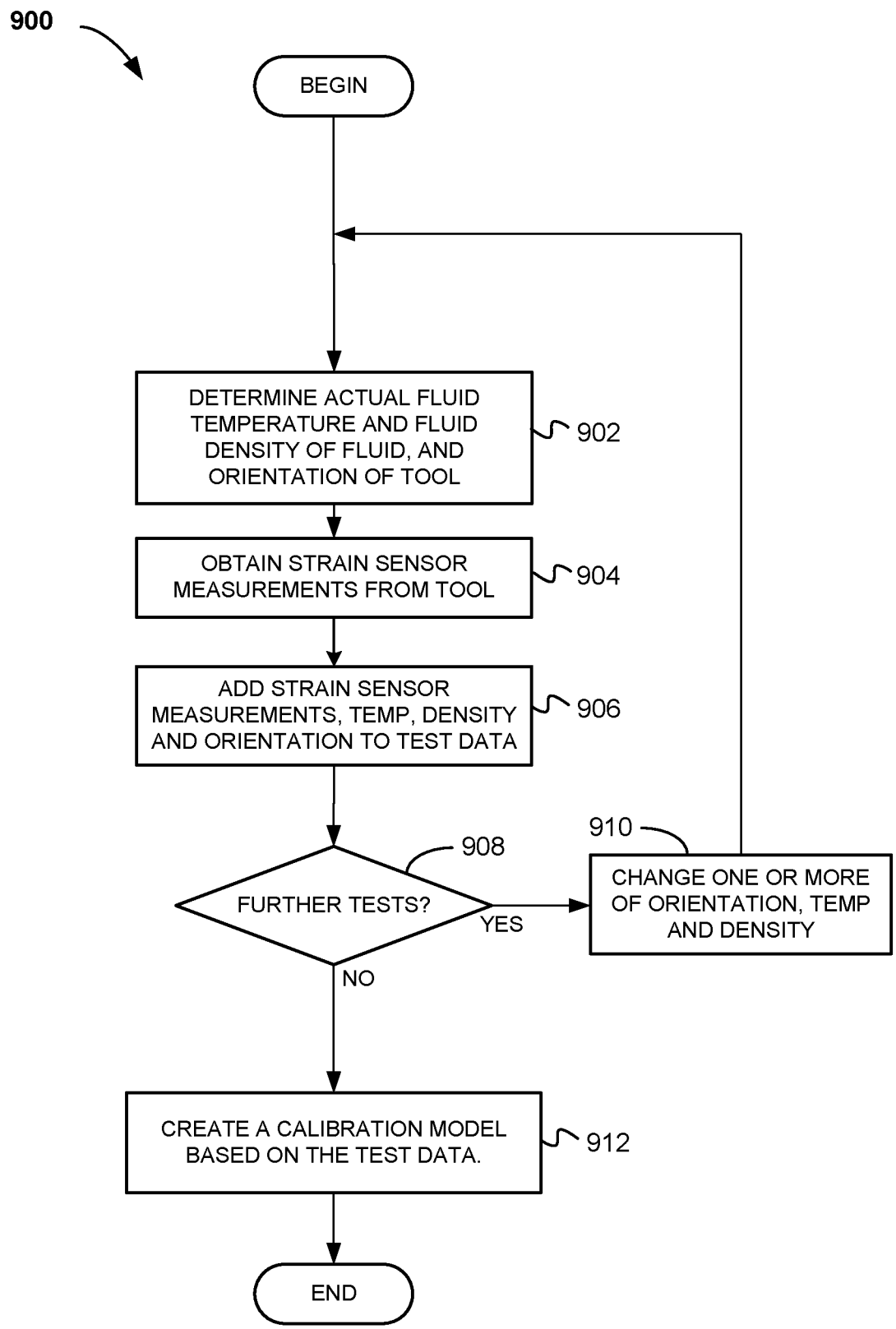
FIG. 9 depicts a flowchart of operations to calibrate a strain sensor-based tool to measure downhole fluid density, according to some embodiments.
Figure 10:
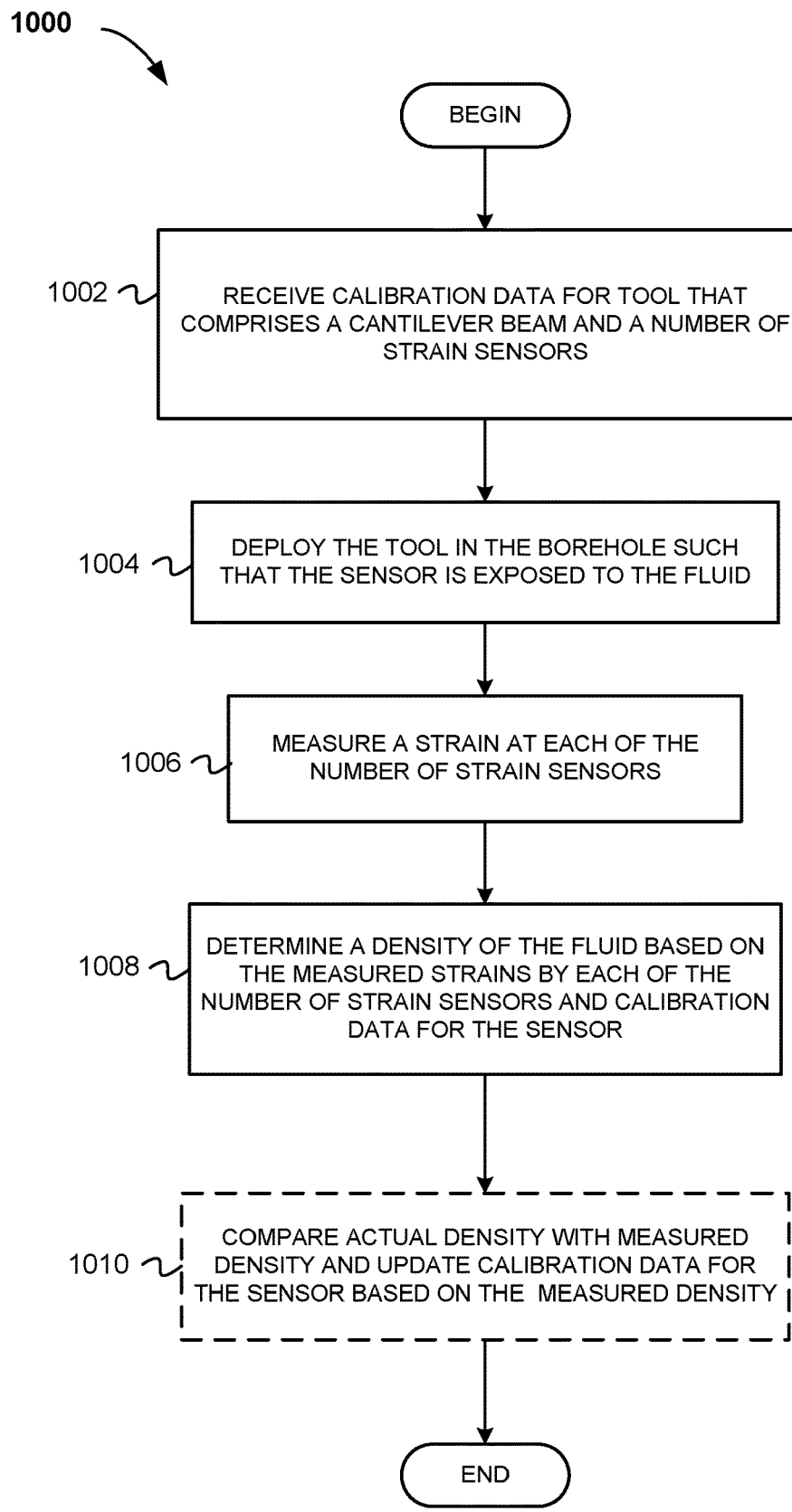
FIG. 10 depicts a flowchart of operations to measure downlink fluid density using a calibrated strain sensor-based tool, according to some embodiments.

FIGS. 9 and 10 provide example operations for calibrating a strain sensor-based tool and measuring downhole fluid density. The flowcharts described below include operations that can be performed by hardware, software, firmware, or a combination thereof. For example, the operations can be performed by a processor executing program code or instructions.

FIG. 9 depicts a flowchart of operations to calibrate a strain sensor-based tool to measure downhole fluid density, according to some embodiments.

At block 902, a reference density and temperature of a fluid are obtained. The reference density can be obtained by receiving a value for a known density of the fluid, or the reference density can be obtained by receiving a value from a reference device (i.e., a device that is known to produce correct density values). In addition, the current orientation of the tool can be obtained.

At block 904, measurements from a fluid density measurement tool under test are obtained. The measurements may be values obtained from strain sensors on the tool under test.

At block 906, the strain sensor measurements, values derived from the strain sensor measurements (e.g., Von Mises stress values), the fluid temperature, and the reference fluid density can be added to a test data set. In some aspects, the current orientation of the tool can be added to the test data set.

At block 908, a check is made to determine if further tests are to be performed. If no further tests are to be performed, the method proceeds to block 912. If further tests are to be performed, the method proceeds to block 910.

At block 910, one or more testing parameters are changed. For example, the temperature of the test fluid may be changed. As another example, the orientation of the fluid density measurement tool under test may be changed. For instance, the tool may be rotated, tilted or otherwise reoriented in the test fluid. As a further example, the test fluid may be changed to a fluid having a different density. Any combination of one or more parameters may be changed. After the change of the test parameters has been completed, the method returns to block 902 to perform the operations of block 902-908 to obtain further test data based on the changed parameters. For example, the changes will typically cause changes to the stress sensor values or values derived from the stress sensor values (e.g., Von Mises stress values).

Block 912 is reached after all desired tests have been performed. At block 912, calibration data is created based on the test data created by the previous iterations of blocks 902-908. In some embodiments, the calibration data can be a machine learning model that is created by applying machine learning algorithms to the test data. The machine learning algorithms can parse the data, discover relationships in the data and produce a learned algorithm that is based on input data and the discovered relationships. Input data can be provided to the model, and using the discovered relationships, the model can apply the learned algorithm to provide output data. For example, the machine learning algorithm can discover relationships between the strain sensor values and/or values derived from the strain sensor values (e.g., Von Mises stresses) and provide a fluid density value or temperature value. The machine learning algorithm can be a deep learning algorithm that includes layers in an artificial neural network. The neural network can be trained using the test data to make decisions regarding fluid density values and temperature values based on input values such as strain sensor values and/or values derived from the strain sensor values (e.g., Von Mises stresses).

Machine learning methods such as those illustrated in FIG. 9 can be used to calibrate a strain sensor-based fluid density measurement tool. However, other methods are possible and within the scope of the inventive subject matter. For example. Finite Element Analysis (FEA) methods can be used to calibrate the fluid density measurement tool. FEA can be used to analyze the structure of the fluid density measurement tool and the materials used in the tool to determine calibration data for the tool.

FIG. 10 depicts a flowchart 1000 of operations to measure downhole fluid density using a calibrated strain sensor-based tool, according to some embodiments. As an example, the calibrated strain sensor-based tool can be calibrated according to the methods described above. The flowchart 1000 includes operations that can be performed by hardware, software, firmware, or a combination thereof. For example, the operations can be performed by a processor executing program code or instructions.

At block 1002, calibration data is received for the strain sensor-based tool. In some embodiments, the calibration data comprises a calibration model that is learned utilizing machine learning algorithms. Further, the calibration data can include an artificial neural network that has been trained using machine learning techniques.

At block 1004, the tool is deployed in a borehole such that the strain sensor-based tool is exposed to a fluid in the borehole. In some embodiments, the tool can be deployed as a part of a wellbore tubular assembly. In alternative embodiments, the tool can be deployed as part of, or attached to, a drill string. The fluid can be any type of fluid, examples which include, hut are not limited to drilling fluids, completion fluids, production fluids, formation fluids, etc.

At block 1006, a strain value at each of a number of strain sensors of the strain sensor-based measurement tool is measured while the tool is in the borehole and the tool is exposed to the fluid.

At block 1008, a density of the fluid is determined based on the measured strains by each of the number of strain sensors and the calibration data for the tool. For example, the strain values returned by the strain sensors can be used as input for a machine-learned model and the current fluid density is an output of the model. As another example, a value derived from the strain sensor values can be used as input to the machine-learned model. For example, maximum and minimum Von Mises stress values can be derived from the strain sensor values and used as input to the machine-learned model.

As noted above, the fluid density can be used to control other aspects of the operation of a wellbore system. For example, the fluid density may be used to determine a choke setting of a downhole choke. In some embodiments, block 1012 can be optionally performed. At block 1012, the actual density of a fluid from the wellbore can be determined. For example, in the case of completion fluids, the density of the completion fluid is typically known because completion fluids are circulated into the wellbore and the density can be determined prior to such circulation into the wellbore. In the case of fluids produced from the wellbore, a sample of the fluid can be taken after it reaches the surface, and the actual density can be determined. The actual density can be compared to the density value determined from the measurements received from the tool and the calibration data. The calibration data can be adjusted based on any differences in the actual density and the density as determined from the fluid density measurement tool, thus recalibrating the tool.

In addition to, or instead of fluid density, the fluid density measurement tool 126 and 800 can provide a temperature at the location of the strain sensor. As discussed above, temperature is one of the parameters used to calibrate the fluid density measurement tool. Further, the strain sensors exhibit a voltage drop that correlates with the temperature at the strain sensor. Thus, parameters that correlate the voltage of the strain sensor with temperature can be included in the calibration data 152 and used to provide a current temperature during operational phases a the fluid density measurement tool 126 and 800.

In some embodiments, the weighted rod portion or weighted tail portion of the fluid density measurement toot has a specific gravity (S.G.) of less than two. Having a low density of less than two S.G. can make the tool more responsive to changes in fluid density.

Figure 11:
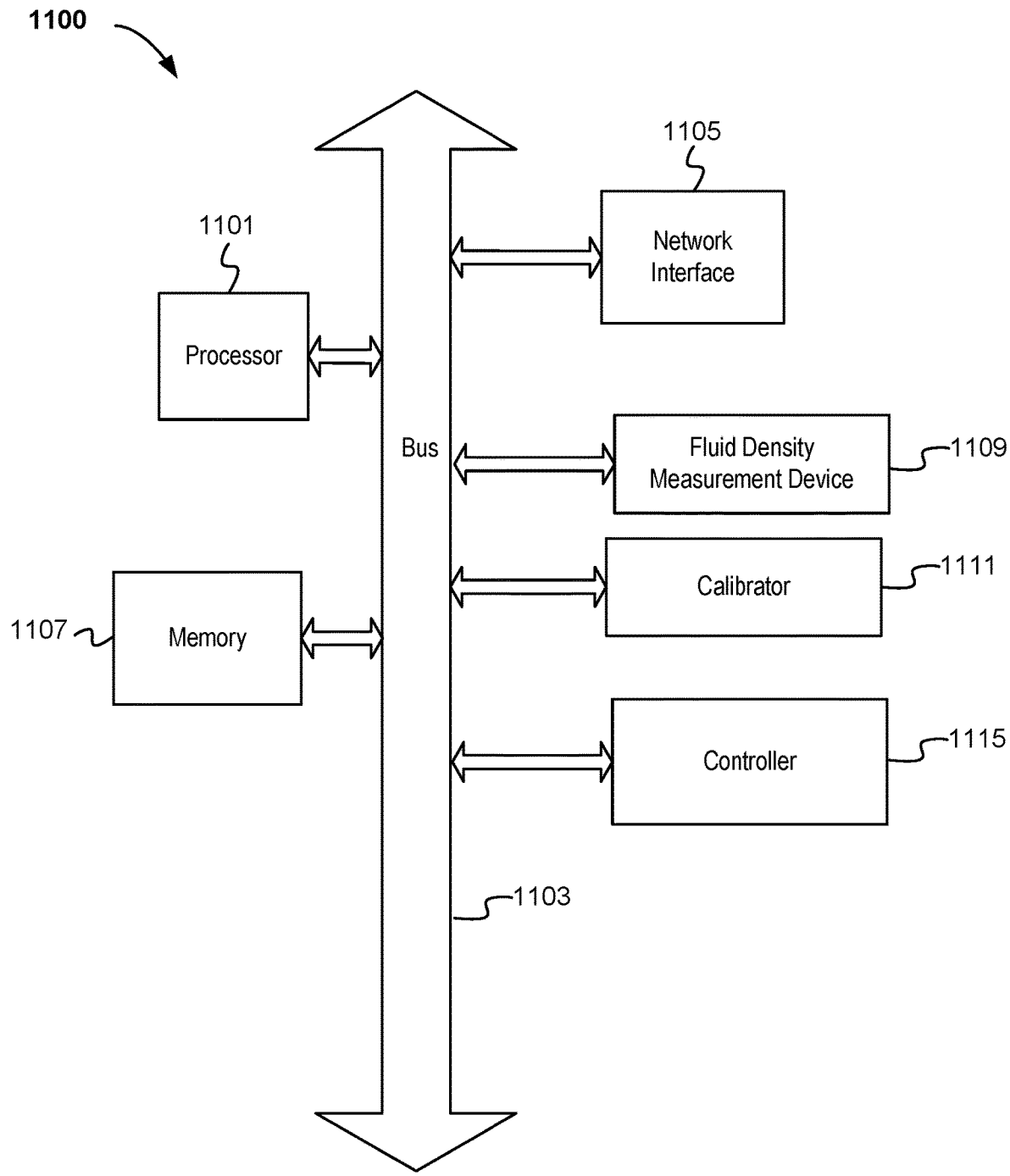
FIG. 11 depicts an example computer system according to some embodiments.

FIG. 11 depicts an example computer system 1100 according to some embodiments. The computer includes a processor 1101 (possibly including multiple processors, multiple cores, multiple nodes, and/or implementing multi-threading, etc.). The computer includes memory 1107. The memory 1107 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 1103 (e.g., PCI, ISA, PCI-Express, Hyper-Transport® bus, InfiniBand® bus, NuBus, etc.) and a network interface 1105 (e.g., a Fiber Channel interface, an Ethernet interface, an internet small computer system into face, SONET interface, wireless interface, etc.).

The computer also includes a fluid density measurement device 1109, a calibrator 1111 and a controller 1115. The fluid density measurement device 1109 can perform operations for measurement or determination of fluid density (as described above). The calibrator 1111 can perform operations to calibrate a fluid density measurement tool (as described above). The controller 1115 can control different operations that can occur in the response to results from measurement of the fluid density. For example, the controller 1115 can communicate instructions to the appropriate equipment, devices, etc. to alter cementing operations, drilling operations, fracturing operations, etc. Any one of the previously described functionalities may be partially (or entirely) implemented in hardware and/or on the processor 1101. For example, the functionality may be implemented with an application specific integrated circuit, in logic implemented in the processor 1101, in a co-processor on a peripheral device or card, etc. Further, realizations may include fewer or additional components not illustrated in FIG. 11 (e.g., video cards, audio cards, additional network interfaces, peripheral devices, etc.). The processor 1101 and the network interface 1105 are coupled to the bus 1103. Although illustrated as being coupled to the bus 1103, the memory 1107 may be coupled to the processor 1101.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory) a portable compact disc read-only memory (CD-ROM), an optical storage device, a magnetic storage device, or any suitable combination of the foregoing. In the context of this document, a machine-readable storage medium may be any tangible medium that can contain, or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language such as tire Java® programming language. C++ or the like, a dynamic programming language such as Python; a scripting language such as Perl programming language or PowerShell script language; and conventional procedural programming languages, such as the "C" programming language or similar programming languages. The program code may execute entirety on a stand-alone machine, may execute in a distributed manner across multiple machines, and may execute on one machine while providing results and or accepting input on another machine.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fail within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

As used herein, the term "or" is inclusive unless otherwise explicitly noted. Thus, the phrase "at least one of A, B, or C" is satisfied by any element from the set {A, B, C} or any combination thereof, including multiples of any element.

Example embodiments include the following:

Embodiment 1: A method for determining fluid density, the method comprising: receiving calibration data for a fluid density measurement tool, the fluid density measurement tool comprising a cantilever beam and at least one strain sensor that is coupled to the cantilever beam, wherein the cantilever beam is housed in the fluid density measurement tool and is buoyed by a fluid that enters the fluid density measurement tool; measuring strain values at the at least one strain sensor; and determining a density of the fluid based on the calibration data, and the strain values measured at the at least one strain sensor.

Embodiment 1 may further comprise Embodiments 2 through 9 as follows Embodiment 2: The method of embodiment 1, wherein determining the density of the fluid based on the calibration data and the strain values comprises determining the density of the fluid based on one or more values derived from the strain values. Embodiment 3: The method of embodiment 2, wherein the one or more values derived from the strain values comprise Von Mises stress values. Embodiment 4: The method of any of embodiments 1-3. Further comprising generating the calibration data utilizing a machine learning algorithm. Embodiment 5: The method of embodiment 4, wherein the calibration data comprises a machine learning model, and wherein generating the calibration data comprises: exposing the fluid density measurement tool to fluids having varying densities, and at varying ambient property values and at varying orientations of the fluid density measurement tool; storing strain sensor values, ambient property values, and known density values of the fluids as test data and creating the machine learning model based on the test data, the machine learning model correlating the strain sensor values, ambient property values, and known density values. Embodiment 6: The method of embodiment 5, further comprising determining Von Mises stress values from the strain sensor valises and storing the Von Mises stress valises in the test data. Embodiment 7: The method of any of embodiments 5-6, wherein the varying ambient properties comprise an ambient temperature. Embodiment 8: The method of any of embodiments 1-7, further comprising updating the calibration data after deployment of the fluid density measurement tool in a wellbore. Embodiment 9: The method of embodiment 8, wherein updating the calibration data comprises adjusting the calibration data based on comparing the density of the fluid as determined from the calibration data to a density of the fluid determined after the fluid sampled at a surface of the wellbore.

Embodiment 10: An apparatus comprising: a fluid density measurement tool, the fluid density measurement tool comprising a cantilever beam and at least one strain sensor that is coupled to the cantilever beam, wherein the cantilever beam is located in the fluid density measurement tool; a processor communicably coupled to the fluid density measurement tool; and a machine-readable medium having program code executable by the processor to cause the apparatus to, receive calibration data for the fluid density measurement tool, receive measurements of strain values at the at least one strain sensor, and determine a density of a fluid based on the calibration data, and the strain values measured at the at least one strain sensor.

Embodiment 10 may further comprise Embodiments 11 through 15 as follows. Embodiment 11: The apparatus of embodiment 10, wherein the cantilever beam is located in a chamber formed within a housing of the fluid density measurement tool, wherein the housing includes an opening to allow the fluid to enter the chamber of the fluid density measurement tool. Embodiment 12: The apparatus of any of embodiment 10-11, wherein the program code to determine the density of the fluid based on the calibration data and the strain values comprises program code to determine the density of the fluid based on one or more values denied from the strain values. Embodiment 13: The apparatus of embodiment 12, wherein the one or more values derived front the strain values comprise Von Mises stress values. Embodiment 14: The apparatus of any of embodiments 10-13, wherein the program code farther comprises program code to update the calibration data after deployment of the fluid density measurement tool in a wellbore. Embodiment 15: The apparatus of embodiment 14, wherein the program code to update the calibration data comprises program code to adjust the calibration data based on a comparison of the density of the fluid as determined from the calibration data to a density determined from a sample of the fluid obtained at a surface of the wellbore.

Embodiment 16: One or more non-transitory machine-readable media comprising program code for determining a third density, the program code to: receive calibration data for a fluid density measurement tool, the fluid density measurement tool comprising, a cantilever beam and at least one strain sensor that is coupled to the cantilever beam, wherein the cantilever beam is housed in the fluid density measurement tool; measure strain values at the at least one strain sensor; and determine a density of a fluid based on the calibration data, and the strain values measured at the at least one strain sensor.

Embodiment 16 may further comprise Embodiments 17 through 20 as follows. Embodiment 17: The one or more non-transitory machine-readable media of embodiment 16, wherein the program code to determine the density of the fluid based on the calibration data and the strain values comprised program code to determine the density of the fluid based on one or more values derived from the strain values. Embodiment 18: The one or more non-transitory machine-readable media of embodiment 17, wherein the one or more values derived from the strain values comprise Von Mises stress values. Embodiment 19: The one or more non-transitory machine-readable media of any of embodiments 16-18, wherein the program code further comprises program code to generate the calibration data utilizing a machine learning algorithm. Embodiment 20: The one or more non-transitory machine-readable media of embodiment 19, wherein the calibration data comprises a machine learning model, and wherein program code to determine the calibration data comprises program code to: store strain sensor values, ambient property values, and known density values of the fluids as test data obtained from the fluid density measurement tool, and create the machine learning model based on the test data, the machine learning model correlating the strain sensor values, ambient property values, and known density values.

What is claimed is:

1. A method for determining fluid density, the method comprising:
   receiving calibration data for a fluid density measurement tool, the fluid density measurement tool comprising a cantilever beam and coupled with at least one strain sensor that is protected from a fluid, wherein the cantilever beam is housed in the fluid density measurement tool and is buoyed by the fluid that enters the fluid density measurement tool;
   measuring, by the at least one strain sensor, strain values indicating a buoyancy force of the fluid on the cantilever beam; and
   determining a density of the fluid based on the calibration data, and the strain values measured by the at least one strain sensor.

2. The method of claim 1, wherein determining the density of the fluid based on the calibration data and the strain values comprises determining the density of the fluid based on one or more values derived from the strain values.

3. The method of claim 2, wherein the one or more values derived from the strain values comprise Von Mises stress values.

4. The method of claim 1, further comprising generating the calibration data utilizing a machine learning algorithm.

5. The method of claim 4, wherein the calibration data comprises a machine learning model, and wherein generating the calibration data comprises:
   exposing the fluid density measurement tool to fluids having varying densities, and at varying ambient property values and at varying orientations of the fluid density measurement tool;
   storing strain sensor values, ambient property values, and known density values of the fluids as test data; and
   creating the machine learning model based on the test data, the machine learning model correlating the strain sensor values, ambient property values, and known density values.

6. The method of claim 5, further comprising determining Von Mises stress values from the strain sensor values and storing the Von Mises stress values in the test data.

7. The method of claim 5, wherein the varying ambient properties comprise an ambient temperature.

8. The method of claim 1, further comprising updating the calibration data after deployment of the fluid density measurement tool in a wellbore.

9. The method of claim 8, wherein updating the calibration data comprises adjusting the calibration data based on comparing the density of the fluid as determined from the calibration data to a density of the fluid determined after the fluid sampled at a surface of the wellbore.

10. An apparatus comprising:
    a fluid density measurement tool, the fluid density measurement tool comprising a cantilever beam and coupled with at least one strain sensor that is protected from a fluid, wherein the cantilever beam is located in the fluid density measurement tool and is buoyed by the fluid that enters the fluid density measurement tool;
    a processor communicably coupled to the fluid density measurement tool; and
    a machine-readable medium having program code executable by the processor to cause the apparatus to,
       receive calibration data for the fluid density measurement tool,
       receive, from the at least one strain sensor, measurements of strain values indicating a buoyancy force of the fluid exerted on the cantilever beam, and
       determine a density of a fluid based on the calibration data, and the strain values measured at the at least one strain sensor.

11. The apparatus of claim 10, wherein the cantilever beam is located in a chamber formed within a housing of the fluid density measurement tool, wherein the housing includes an opening to allow the fluid to enter the chamber of the fluid density measurement tool.

12. The apparatus of claim 10, wherein the program code to determine the density of the fluid based on the calibration data and the strain values comprises program code to determine the density of the fluid based on one or more values derived from the strain values.

13. The apparatus of claim 12, wherein the one or more values derived from the strain values comprise Von Mises stress values.

14. The apparatus of claim 10, wherein the program code further comprises program code to update the calibration data after deployment of the fluid density measurement tool in a wellbore.

15. The apparatus of claim 14, wherein the program code to update the calibration data comprises program code to adjust the calibration data based on a comparison of the density of the fluid as determined from the calibration data to a density determined from a sample of the fluid obtained at a surface of the wellbore.

16. One or more non-transitory machine-readable media comprising program code for determining a fluid density, the program code to:
    receive calibration data for a fluid density measurement tool, the fluid density measurement tool comprising a cantilever beam and coupled with at least one strain sensor that is protected from a fluid, wherein the cantilever beam is housed in the fluid density measurement tool and is buoyed by the fluid that enters the fluid density measurement tool;
    measure strain values indicating a buoyancy force of the fluid exerted on the cantilever beam; and
    determine a density of a fluid based on the calibration data, and the strain values measured at the at least one strain sensor.

17. The one or more non-transitory machine-readable media of claim 16, wherein the program code to determine the density of the fluid based on the calibration data and the strain values comprised program code to determine the density of the fluid based on one or more values derived from the strain values.

18. The one or more non-transitory machine-readable media of claim 17, wherein the one or more values derived from the strain values comprise Von Mises stress values.

19. The one or more non-transitory machine-readable media of claim 16, wherein the program code further comprises program code to generate the calibration data utilizing a machine learning algorithm.

20. The one or more non-transitory machine-readable media of claim 19, wherein the calibration data comprises a machine learning model, and wherein program code to determine the calibration data comprises program code to:

store strain sensor values, ambient property values, and known density values of the fluids as test data obtained from the fluid density measurement tool; and create the machine learning model based on the test data, the machine learning model correlating the strain sensor values, ambient property values, and known density values.

\* \* \* \* \*